United States Patent [19]

Holtkamp, Sr.

[11] Patent Number: Plant 6,532

[45] Date of Patent: Jan. 10, 1989

[54] AFRICAN VIOLET PLANT NAMED DENVER

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 56,412

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An African violet plant named Denver, characterized by its profuse flowering, and very pure white flowers; strong upright flower stem curving toward the center; vigorous growth habit; bright green girl type velvet leaves with light green center; and long lasting and non-dropping flowering habit.

1 Drawing Sheet

The present invention comprises a new and distinct cultivar of African violet plant, botanically known as *Saintpaulia ionantha,* and hereinafter referred to by the cultivar name Denver.

The new cultivar Denver is a mutation and was discovered by applicant in 1985 in Haffen, Federal Republic of Germany, while growing as a single plant among plants of the parent cultivar Atlanta, disclosed in U.S. Plant Pat. No. 4,875. The new cultivar was immediately recognized by its pure white flower color, as compared to the light rose flower color of its parent, and was given the selection number M349 weis. The parent cultivar Atlanta was developed in a breeding program in Isselburg, Federal Republic of Germany from a female parent identified as XIX 34 pink girl and a male parent identified as XXII 148.

Asexual reproduction of the new cultivar by leaf cuttings, as performed by me at Haffen, Federal Republic of Germany, has demonstrated that the combination of characteristics as herein disclosed for Denver are firmly fixed and retained through successive generations of asexual reproduction.

Denver has not been observed under all possible environmental conditions. The phenotype may vary significantly with variations in environment such as temperature, light intensity and day length. The following observations, measurements and values describe the new cultivar as grown in a 10 cm pot in Haffen, Federal Republic of Germany and Nashville, Tenn. under greenhouse conditions which closely approximate those generally used in commercial practice.

The following traits have been repeatedly observed and are determined to be basic characteristics of Denver which in combination distinguish this african violet as a new and distinct cultivar:

1. Strong upright flower stems curving toward the center.
2. Girl-type leaves, being generally cup-shaped with a contrasting, light green center which radiates along the veins.
3. After maturity the flowers dry off, and remain on the peduncle without becoming infected by botrytis.
4. Profuse flowering, and very pure white flowers.
5. Each plant carries 7–9 and more upright flower stems, each of which carries 10–14 flowers.
6. Vigorous grower.
7. Plant saleable 9 to 10 weeks after potting.

8. Bright green velvet leaves with light green center, slightly hairy.
9. Long-lasting, non-dropping single flowers are violet shaped but slightly wavy.
10. Seed capsule pushes slightly through.
11. The girl-type leaves are strongly serrated.

The new cultivar is most similar to the parent cultivar Atlanta, being similar thereto in many respects. Denver is principally distinguished from by its pure white flower color.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 2:00 p.m. in Nashville, Tenn.

Botanical classification: *Saintpaulia ionantha,* Ramat., cv. Denver.

Propagation: The new cultivar holds its distinguishing characteristics through successive propagations by leaf cuttings and by division of shoots.

Plant: From 9–10 cm tall when grown in pots, and approximately 18–20 cm in diameter when fully grown. The growth rate is vigorous.

*Leaves.*—Shape: Round, girl-type, curled up at the center. Diameter: 65–75 mm. Texture: Velvety, shiny. Aspect: Indentations (especially the younger leaves), strongly serrated, slightly hairy, bright light green center radiating along the veins. Ribs and veins: Upperside well visible, light green towards the center; underside very well pronounced, very light green, shiny, slight purplish touch in between the veins. Color (upper side): Yellow green 147A. Color (under side): Yellow green 146C. Petioles: Strong, upright, very light green, hairy.

*Flowers.*—Buds: Bell-shaped, 6–8 mm just before opening. Sepals: Five (5) in number, purplish-brown. Calyx: Funnel-shaped. Aspect: Spear-shaped, hairy. Peduncle: Strong, upright, purplish brown, hairy.

*Individual flowers.*—Size: 40–45 mm. Shape: Single violet-shaped; 3 large and 2 small petals. Color (upper side): Pure white 155D. Color (under side): Pure white. Borne: Each flower stem carries 10–14 flowers on relatively thin peduncles that are free standing above the leaves, curving toward the center of the plant Flowering habit: Flowers 9–10 weeks after potting. Corolla: Compact flower head, free standing above the leaves.

*Reproductive organs.*—Stamens: Two (2) in number. Anthers: Two stamens composed of 4 anther cells. Filaments: 5–6 mm long, yellowish green. Pollen Color: Yellow 7A. Styles: 6–7 mm, with a light green, hairy base of ovary.

*Roots.*—Normally developed, white when young, turning slightly brownish when older.

Disease resistance: Good.

General observations: Denver has a very attractive appearance due to its bright green girl-type leaves above which appears a pure white compact flower head. The flowers are carried on strong upright flower stems and are free standing above the leaves. The flowers are long-lasting and non-dropping, and flowering is profuse.

I claim:

1. A new and distinct cultivar of African violet named Denver, as described and illustrated, and particularly characterized by its profuse flowering, and very pure white flowers; strong upright flower stems curving toward the center; vigorous growth habit; bright green girl type velvet leaves with light green center; and long lasting and non-dropping flowering habit.

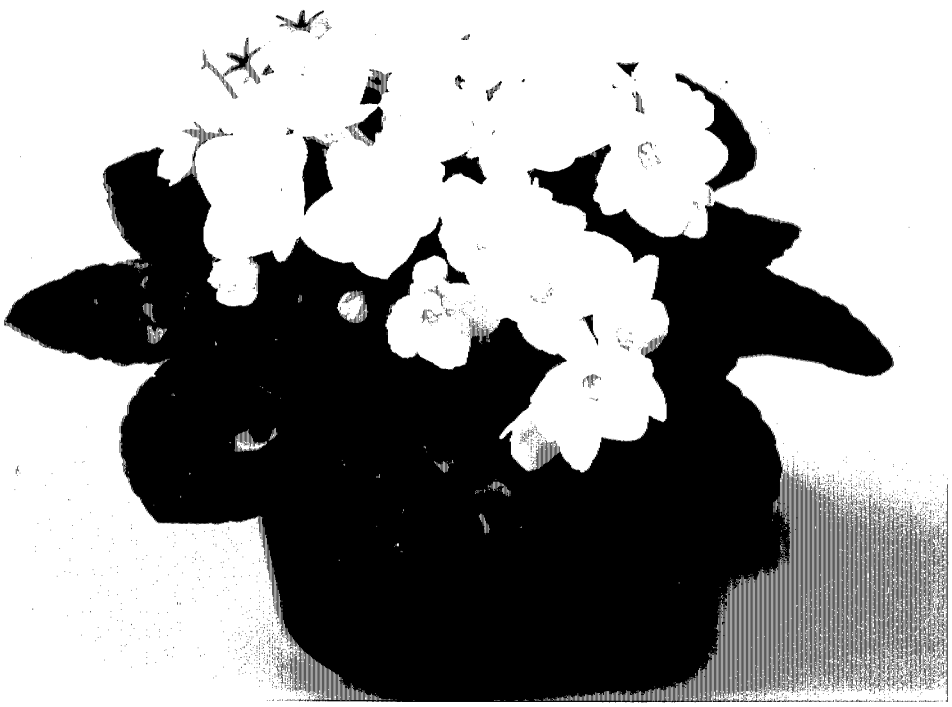

* * * * *